United States Patent

Otsu et al.

[11] Patent Number: 5,880,142
[45] Date of Patent: Mar. 9, 1999

[54] TERMITE-CONTROLLING AGENT COMPOSITION

[75] Inventors: Yuichi Otsu, Tochigi; Shinzaburo Sone, Ibaraki, both of Japan

[73] Assignee: Nihon Bayer Agrochem K.K., Tokyo, Japan

[21] Appl. No.: 848,007

[22] Filed: Apr. 28, 1997

Related U.S. Application Data

[62] Division of Ser. No. 532,299, Sep. 22, 1995, Pat. No. 5,661,164.

[30] Foreign Application Priority Data

Sep. 30, 1994 [JP] Japan ................................ 6-259634

[51] Int. Cl.$^6$ ............................ A01N 37/34; A01N 43/40
[52] U.S. Cl. ............................................ 514/357; 514/521
[58] Field of Search ...................... 514/357, 521

[56] References Cited

U.S. PATENT DOCUMENTS

| | | | |
|---|---|---|---|
| 4,742,060 | 5/1988 | Shiokawa et al. | 514/252 |
| 5,032,589 | 7/1991 | Shiokawa et al. | 514/245 |
| 5,051,434 | 9/1991 | Kozo et al. | 514/357 |
| 5,175,301 | 12/1992 | Minamida et al. | 546/272 |
| 5,214,152 | 5/1993 | Minamida et al. | 548/181 |
| 5,304,566 | 4/1994 | Ishimitsu et al. | 514/357 |

FOREIGN PATENT DOCUMENTS

| | | |
|---|---|---|
| 149005 | 7/1985 | European Pat. Off. . |
| 428941 | 11/1990 | European Pat. Off. . |

OTHER PUBLICATIONS

Worthing et al, The Pesticide Manual, 9$^{th}$ Ed. (1991) pp. 198–199.
Haas, et al. C.A.; vol. 114, (1991) 114:201780a.
Tsuboi, et al., C.A.; vol. 109, (1988) 109:124,423d.

*Primary Examiner*—Allen J. Robinson
*Attorney, Agent, or Firm*—Sprung Kramer Schaefer & Briscoe

[57] ABSTRACT

Combating termites with a composition comprising
(a) at least one compound of the formula

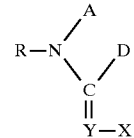

wherein,
R denotes a hydrogen atom, acyl, alkyl or optionally substituted heteroarylalkyl,
A denotes a hydrogen atom, alkyl or a bivalent group which binds to B,
D denotes alkyl, —S—R$^1$,

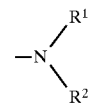

or bivalent group or atom which binds to A.
wherein R$^1$ or R$^2$ each independently denotes a hydrogen atom, acyl, alkyl or optionally substituted heteroarylalkyl.
Y denotes =N— or

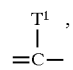

wherein T$^1$ denotes a hydrogen atom or optionally substituted alkyl, and
X denotes an electron attracting group,
and
(b) a pyrethoid compound,

2 Claims, No Drawings

TERMITE-CONTROLLING AGENT COMPOSITION

This application is a divisional, of application Ser. No. 08/532,299, filed Sep. 22, 1995 now U.S. Pat. No. 5,661,164.

The present invention relates to a termite-controlling agent. In more detail, the invention relates to a termite-controlling agent composition showing a synergistic effect, which contains a particular permeable insecticidal compound and a pyrethroid compound.

It is already known, as disclosed, for example, in Japanese Laid-Open Patent Publication Nos. 267575/1986, 235881/1990, 154741/1992, 288859/1990 and 171/1990, Japanese Patent Publication No. 776/1994, that nitromethylene, nitroimino and cyanoimino compounds have excellent insecticidal activity in the field of plant protection. It is further known, as disclosed in Japanese Laid-Open Patent Publication Nos. 56612/1994 and 107510/1994, that these compounds show excellent insecticidal activity as a termite-controlling agent. It is further disclosed in Japanese Laid-Open Patent Publication No. 126805/1988 that a mixed agent of a particular nitroimino compound and a pyrethroid compound has excellent activity as an agrohorticultural insecticide.

On the other hand, chlordane had hitherto been used frequently as a termite-controlling agent in various fields in Japan but its use was prohibited in view of its long-term residual activity and its influence on the environment. Therfore, the chemicals now being used are, mainly, organophosphorus insecticides such as phoxim (chemical name: O-(α-cyanobenzylideneamino) O,O-diethyl-phosphorothioate) and chlorpyrifos (chemical name: O,O-diethyl 3,5,6-trichloro-2-pyridyl-phosphorothioate), and pyrethroid insecticides such as permethrin (chemical name: 5-benzyl-3-furylmethyl 3-(2-methoxy -carbonyl-1-propenyl)-2,2-dimethyl-cyclopropanecarboxylate) and decamethrin (chemical name: α-cyano3-phenoxy-benzyl d,l-cis-3-(2,2-dibromovinyl)-2,2-dimethyl- cyclopropanecarboxylate).

However, these chemicals are not satisfactory because there are limitations on use, concentration, the number of times of treatment, safety, effect on wooden houses (residences), and the like, etc.

The present invention provides termite-controlling agents without such drawbacks; viz. a composition containing effective amounts a compound of the formula

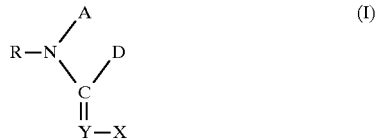 (I)

wherein,
R denotes a hydrogen atom, acyl, alkyl or optionally substituted heteroarylalkyl,
A denotes a hydrogen atom, alkyl or a bivalent group which binds to B,
D denotes alkyl, —S—$R^1$,

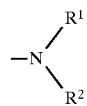

or a bivalent group or atom which binds to A,
wherein $R^1$ and $R^2$ each independently denotes a hydrogen atom, acyl, alkyl or optionally substituted heteroarylalkyl, Y denotes =N— or

Wherein $T^1$ denotes a hydrogen atom or optionally substituted alkyl, and
X denotes an electron attracting group,
and
(b) a pyrethroid compound, Surprisingly, the termite-controlling agent compositions of the invention containing a combination of a compound (a) of the above formula (I) with a pyrethroid compound (b) as an effective ingredient display remarkable synergy and exhibits excellent termite-control at a low concentration which is ineffective for each component used alone, In the compounds of the above formula (I) used as an effective ingredient in the composition of the invention, the term "acyl" means, in the broad sense, an acyl group derived from an organic carbonic acid or an organic sulfonic acid, and includes, specifically for example, formyl; alkylcarbonyls such as acetyl and propionyl; arylcarbonyls such as benzoyl; alkylsulfonyls such as methylsulfonyl and ethylsulfonyl, etc.;

"alkyl" can either be straight-chain or branched chain, and includes, for example, methyl, ethyl, propyl, isopropyl, butyl, isobutyl, sec-butyl, tert-butyl, pentyl, isoamyl, hexyl, heptyl, octyl, 2-ethylhexyl, decyl, dodecyl, etc., and preferably lower alkyls having up to 6, particularly up to 4 carbon atom;

the heteroaryl in the "heteroarylalkyl" is a monocyclic group having at least one hetero atom selected from N, O and S atoms, preferably at least one N atom, and examples of such aromatic heterocyclic groups are thiazolyl, isothiazolyl, pyrazolyl, imidazolyl, oxazolyl, isoxazolyl, pyridyl, pyrimidyl, pyrazyl, pyridazinyl, etc;

the heteroaryl can optionally be substituted, twice or preferably once by, for example, halogen atoms such as fluoro and chloro, alkyl groups such as methyl and ethyl, haloalkyls such as trifluoromethyl and difluoromethyl, alkoxy groups such as methoxy and ethoxy, haloalkoxy groups such as trifluoromethoxy and 2,2,2-trifluoroethoxy, etc.

As the "bivalent group" in the case where the group A denotes "a bivalent group which binds to B" there can be mentioned $C_{2-4}$alkenylene groups such as ethylene, propylene, trimethylene and 1-methyltrimethylene, and the group

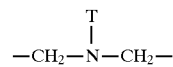

wherein T denotes a hydrogen atom, an alkyl group or an alkylcarbonyl group.

On the other hand, in the case where the group A denotes the above bivalent group, the group B denotes "a bivalent group or atom which binds to A", and thereby the group B combines together with the group A and the carbon atom and nitrogen atom to which these groups bind, to form a nitrogen-containing heterocyclic ring such as, for example, imidazolidine, thiazolidine, tetrahydropyrimiidine, piperidine, 2H-1,3-thiazine and hexahydro-1,3,5-triazine. Thus, the "bivalent group or atom" which can be denoted by the group B includes methylene,

and —S—, etc.

wherein T denotes a hydrogen atom, an alkyl group or an alkylcarbonyl group,

The possible substituent in "optionally substituted alkyl" which can be denote by $T^1$ includes, for example, halogen such as fluorine, chlorine and bromine; hydroxy; alkoxy such as methoxy and ethoxy; alkylthio such as methylthio and ethylthio; alkenylthio such as allylthio; cyano; mono- or di-alkylamino such as methyl-amino, ethylamino, dimethylamino and diethylamino; alkylcarbonyl; such as acetyl and propionyl; alkoxy-carbonyl such as methoxycarbonyl and ethoxycarbonyl; etc.

The "electron attracting group" denoted by the group X includes, for example, nitro; cyano; acyl optionally substituted with halogen, such as acetyl, trichloroacetyl and trifluoroacetyl; alkylsulfonyl optionally substituted with halogen, such as methyl-sulfonyl and trifluoromethylsulfonyl; etc.

Thus, preferred compounds among the compounds of the above formula (I) are compounds wherein, R denotes a hydrogen atom, formyl, $C_{1-4}$ alkylcarbonyl, benzoyl, $C_{1-4}$ alkylsulfonyl, $C_{1-6}$ alkyl or up to 6-membered heteroarylmethyl which has at least one N atom, can optionally have further hetero atom(s) and can optionally be substituted, A denotes a hydrogen atom, $C_{1-6}$ alkyl, ethylene, trimethylene or

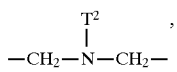

wherein $T^2$ denotes a hydrogen atom, $C_{1-4}$ alkyl or $C_{1-4}$ alkylcarbonyl, D denotes $C_{1-6}$alkyl,—S—$R^{11}$,

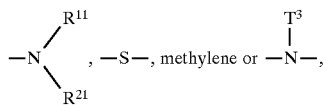

wherein $R^{11}$ and $R^{12}$ each independently denotes a hydrogen atom, formyl, $C_{1-4}$ alkylcarbonyl, benzoyl, $C_{1-4}$ alkylsulfonyl, $C_{1-6}$ alkyl or up to 6-membered heteroarylmethyl which has at least one N atom, can optionally have further hereto atom(s) and can optionally be substituted, and $T^3$ denotes a hydrogen atom, $C_{1-4}$ alkyl or $C_{1-4}$ alkylcarbonyl, Y denotes =N— or =CH—, and X denotes nitro or cyano.

Further preferred compounds among the compounds of the formula (I) are compounds wherein, R denotes a hydrogen atom, formyl, acetyl, $C_{1-4}$ alkyl, 2-chloro-5-pyridylmethyl or 2-chloro-5-thiazolyl, A denotes a hydrogen atom, $C_{1-4}$ alkyl, ethylene trimethylene or

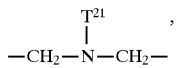

herein $T^{21}$ denotes methyl or ethyl,

D denotes $C_{1-4}$alkyl,—S—$R^{12}$,

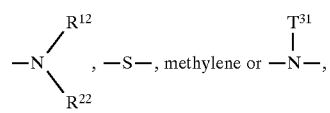

herein $R^{12}$ and $R^{22}$ each denote a hydrogen atom, formyl, acetyl, $C_{1-4}$ alkyl, 2-chloro-5-pyridylmethyl or 2-chloro-5-thiazolyl, and $T^{31}$ denotes methyl or ethyl, Y denotes =N— or=CH—, and X denotes nitro or cyano.

Particularly preferred compounds among the compounds of the formula (I) are compounds wherein, R denotes 2-chloro-5-pyridylmethyl or 2-chloro-5-thiazolylmethyl, A denotes a hydrogen atom, $C_{1-4}$ alkyl, ethylene, trimethylene or

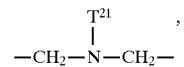

herein $T^{21}$ denotes methyl or ethyl,

B denotes $C_{1-4}$ alkyl, —S—$R^{13}$,

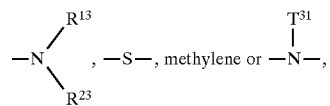

herein $R^{13}$ and $R^{23}$ each denote a hydrogen atom, methyl, ethyl, 2-chloro-5-pyridylimethyl or 2-chloro-5-thiazolylmethyl, and $T^{31}$ denotes methyl or ethyl, Y denotes =N— or =CH—, and X denotes nitro or cyano.

Preferred specific examples of the compounds of the formula (I) used as one of the effective ingredients in the invention are as follows.

1-(6-chloro-3-pyridylmethyl)-N-nitro-imidazolidin-2-ylideneamine,

N-cyano-N-(2-chloro-5-pyridylmethyl)-N'-methylacetamidine,

1-[N-(6-chloro-3-pyridylmethyl)-N-ethylamino]-1-methylamino-2-nitro-ethylene, 1-(2-chloro-5-pyridylmethyl)-5-methyl-2-nitroimino-hexahydro-1,3,5-triazine, 1-(2-chloro-5-thiazolylmethyl)-3,5-dimethyl-2-nitroimino-hexahydro-1,3,5-triazine, 1-(2-chloro-5-pyridylmethyl)-3,5-dimethyl-2-nitroimino-hexahydro- 1,3,5-triazine, 1-(2-chloro-5-pyridylmethyl)-2-nitromethylene-imidazolidine, 1-[N-(2-chloro-5-thiazolylmethyl)-N-ethylamino]-1-methylamino-2-nitro-ethylene, 3-(2-chloro-5-pyridylmethyl)-2-nitromethylene-thiazolidine, 1-(2-chloro-5-pyridylmethyl)-2-(1-nitro-2-allylthioethylidene) imidazolidine, 1-(2-chloro-5-pyridylmethyl)-2-(1-nitro-2-ethylthioethylidene)imidazolidine, 1-(2-chloro-5-pyridylmethyl)-2-(1-nitro-2-β-methyl-allylthioethylidene) imidazolidine, methyl [3-(2-chloro-5-pyridylmethyl)-1-methyl-2-nitro] guanidinoformate, 1-(2-chloro-5-pyridylmethylamino)-1-methylthio-2-nitroethylene, 1-(2-chloro-5-pyridylmethylamino)-1 methylamino-2-nitroethylene, 1-(2-chloro-5-pyridylmethyl)-3-nitro-2-methylisothiourea, 3-(2-chloro-5-pyridylmethyl)-1-methyl-2-nitroguanidine, 1-(2-chloro-5-pyridylmethylamino)-1-dimethylamino-2-nitroethylene, 1[N-(2-chloro-5-pyridylmethyl)-N-methylamino]-2-methylamino-2-nitro-ethylene, 1-[N-(2-chloro-5-pyridylmethyl)-N-methylamino]1-dimethylamino-2-nitro-ethylene, 3-(2-chloro-5-pyridylmethyl)-1,1-dimethyl-2-nitroguanidine, 1-(2-chloro-5-pyridylmethylamino)-1-ethylamino-2-nitroethylene, 1-amino-1-[N-(2-chloro-5-pyridylmethyl)-N-methylamino]2-nitroethylene, 3-(2-chloro-5-pyridylmethyl)-1,3-dimethyl-2-nitroguanidine, 3-(2-chloro-5-pyridylmethyl)-1,1,3-trimethyl-2-nitroguanidine, 1-amino-1-[N-(2-chloro-5-pyridylmethyl)-N-ethylamino]-2-nitroethylene, 1-[N-(2-chloro-5-pyridylmethl)-N-n-propylamino]-1-methylamino-2-nitro-ethylene, 3-(2-chloro-5-thiazolylmethyl)-1-methyl-2-nitroguanidine, 1-[N-(2-chloro-5-pyridylmethyl)-N-ethylamino]-1-ethylamino-2-nitro-ethylene, and 3-(2-chloro-5-pyridylmethyl)-3-ethyl-1-methyl-2-nitroguanidine, etc.

The compounds of the formula (I) are compounds known per se, disclosed in official gazettes such as Japanese Laid-Open Patent Publication Nos. 267575/1986, 171/1990, 235881/1990, 288859/1990 and 154741/1992, and Japanese Patent Publication No. 776/1994, or compound analogous thereto, and can be prepared by the processes described therein or processes analogous thereto.

On the other hand, the pyrethroid compounds usable together with the foregoing compounds of the formula (I) according to the invention include all natural and synthetic pyrethroid compounds having a pyrethroid-like insecticidal action, and representative examples thereof are as follows (in the following examples, common names and chemical names are mentioned together).

| Common name | Chemical name |
|---|---|
| allethrin: | (±)-3-allyl-2-methyl-4-oxocyclopent-2-enyl(±)cis-trans-chrysanthemate, |
| cyfluthrin: | (RS)-α-cyano-4-fluoro-3-phenoxybenzyl (1RS,3RS)-(1RS,3SR)-3-(2,2-dichlorvinyl)-2,2-dimethylcyclopropanecarboxylate, |
| cypermethrin: | (RS)-α-cyano-3-phenoxybenzyl(1RS,3RS)-(1RS,3SR)-chrysanthemate, |
| decamethrin: | (S)-α-cyano-3-phenoxybenzyl(1R,3R)-3-(2,2-dibromovinyl)-2,2-dimethylcyclopropanecarboxylate, |
| fenpropathrin: | (RS)-α-cyano-3-phenoxybenzyl-2,2,3,3-tetra-methyl-cyclopropanecarboxylate, |
| permethrin: | 3-phenoxybenzyl(1RS,3RS)-(1RS,3SR)-3-(2,2-dichlorovinyl)-2,2-dimethylcyclo-propanecarboxylate, |

-continued

| Common name | Chemical name |
|---|---|
| rethmethrin: | 5-benzyl-3-furylmethyl(±)-cis-trans-chrysanthemate, |
| fluvalinate: | (RS)-α-cyano-3-phenoxybenzyl N-(2-chloro-α,α,α-trifluoro-p-toluyl)-D,L-valinate, |
| tralomethrin: | (S)-α-cyano-3-phenoxybenzyl(1R)-cis-2,2-dimethyl-3-[(RS)-1,2,2,2-tetrabromoethyl]-cyclopropanecarboxylate; |
| fenvalerate: | (RS)-α-cyano-3-phenoxybenzyl-(RS)-2-(4-chlorophenyl)-3-methylbutyrate, |
| silafluofen: | (4-ethoxyphenyl)[3-(4-fluoro-3-phenoxy-phenyl)propyl]dimethylsilane, |
| teflutrin: | 2,3,5,6-tetrafluoro-4-methylbenzyl(2)-(1RS,3RS)-3-(2-chloro-3,3,3-trifluoroprop-1-enyl)-2,2-dimethylcyclopropanecarboxylate, |
| ethofenprox: and bifenthrin: | 2-(4-ethoxyphenyl)-2-methylpropyl 3-phenoxybenzyl ether,3-phenoxybenzyl(1R,3R)-3-(2,2-dichlorovinyl)-2,2-dimethyl-cyclopropanecarboxylate, e.t.c. |

The compounding ratio between the compound (a) of the formula (I) and the pyrethroid compound (b) in the composition of the invention is not strictly limited, and can be varied over a wide range in accordance with the kinds of both ingredients to be combined, etc., but can be in the range of generally 100/1 to 100/100, preferably 100/2 to 100/50 as the weight ratio of the ingredient (a)/the ingredient (b).

The composition of the invention can further contain, if desired, microbicides (fungicides, bactericides, algaecides) to be used for protecting wood, woody plywood, etc. from damage by microorganisms, etc.

Compoundable microbicides (fungicides, bactericides and algaecides) include, for example, those mentioned below:

Trihalosulfenyl compounds such as, for example,
  N-(dichlorofluoromethylthio)-N,N'-dimethyl-N-phenylsulfamide (common name: dichlofluanide),
  N-(dichlorofluoromethylthio)-N',N'-dimethyl-N-P-tolylsulfamide (common name: tolylfluanide),
  N-(trichloromethylthio)phthalimide (common name: folpet),
  N-(dichlorofluoromethylthio)phthalimide (common name: fluorofolpet).

Iodo compounds such as, for example,
  3-iodo-2-propynyl-butyl carbamate (IPBC),
  3-iodo-2-propynyl-hexyl carbamate,
  3-iodo-2-propynyl-cyclohexyl carbamate,
  3-iodo-2-propynyl-phenyl carbamate,
  diiodomethyl-p-tolylsulfone (common name: amical 48) and
  3-bromo-2,3-diiodo-2-propenyl ethyl carbonate.

Phenolic compounds such as, for example
  o-phenylphenol,
  tribromophenol,
  tetrachlorophenol and
  pentachlorophenol.

Azole compounds such as, for example,
  1-(4-chlorophenoxy)-3,3-dimethyl-1-(1H-1,2,4-triazol-1-yl)-2-butanone (common name: triadimefon),
  β-(4-chlorophenoxy)-α(1,1-dimethylethyl)-1H-1,2,4-triazole-1-ethanol (common name: triadimenol),
  ±α[2-(4-chlorophenyl)ethyl]-α-(1,1-dimethylethyl)-1H-1,2,4-triazole-1 - ethanol (common name: tebuconazol),
  1-[2-(2,4-dichlorophenyl)-4-propyl-1,3-dioxolan-2-ylmethyl]-1H-1,2,4-triazole (common name: propiconazol), 1-[2-(2,4-dichlorophenyl)-1,3-dioxolan-2-ylmethyl]-1H-1,2,4-triazole (common name: azaconazol), and
1-{N-propyl-N-[2-(2,4,6-(trichlorophenoxy)ethyl] carbamoyl}imidazole (common name: prochloraz).

Tin compounds such as, for example,
methylene bisthiocyanate (MBT) and
2-thiocyanomethylthiobenzothiazole (TCMTB).

Quaternary ammonium compounds such as, for example,
benzyl-dimethyl-tetradecylammonium chloride and
benzyl-dimethyl-dodecylammonium chloride.

Benzimidazole compounds such as, for example,
2-(2'-furyl)-1H1-benzimidazole (common name: fuberidazole), methyl benzimidazol-2-ylcarbamte (BCM),
2-(4'-thiazolyl)benzimidazole (common name: thiabendazole) and methyl (1-butylcarbamoyl)-2-benzimidazolecarbamate (common name: benomyl).

Isothiazolinone compounds such as, for example,
N-methylisothiazolin-3-one,
5-chloro-N-methylisothiazolin-3-one,
4,5-dichloro-N-octylisothiazolin-3-one and
N-octylisothiazolin-3-one.

Morpholine compounds such as, for example,
$C_{14}$–$C_{11}$-4-alkyl-2,6-dimethylmorpholine (common name: tridemorph).

Pyridine compounds such as, for example,
1-hydroxy-2-pyridine-thione and its sodium iron salt, manganese salt and zinc salt
tetrachloro-4-methylsulfonylpyridine.

N-cyclohexyldiaziniumdioxy compounds such as, for example,
tris-(N-cyclohexyldiaziniumdioxy)aluminum and
bis-(N-cyclohexyldiaziniumdioxy)copper.

Naphthenic acid compounds such as, for example,
zinc naphthenate.

Quinoline compounds such as, for example,
8-hydroxyquinoline copper salt.

and

Nitrile compounds such as, for example,
1,2,3,5-tetrachloro-4,6-cyanobenzene.

The composition of the invention can further contain a synergist, if desired. It is not necessary that the synergist itself is active, and any synergist will do so long as it synergizes at least one of the active ingredients to reinforce the action of the active ingredient.

Examples of these synergists are as follows.

| Common name | Chemical name |
| --- | --- |
| Sesamex | 4-[1-[2-(2-ethoxyethoxy)ethoxy]ethoxy]-1,2-methylene-dioxybenzene, |
| Sulfoxide: | 2-(1,3-benzodioxy-5-yl)=ethyloctyl sulfoxide, |
| Piprotal: | 5-[bis[2-[(2-butoxyethoxy)=ethoxy]methyl]-1,3-benzodioxole, |
| Sesasmolin: | 1,3-benzodioxol-5-yl(1R,3aR,4S,6aR)-4-(1,3-benzodioxol-5-yl)perhydrofuro[3,4-c]furan-1-yl ether, |
| Sesamine: | 1,4-di-(1,3-benzodioxol-5-yl)tetrahydrofuro[3,4-c]furan, |
| Safroxan: | 4-(3,4-methylenedioxyphenyl-5-methyl-m-dioxane |
| Safroxane: | 4-(3,4-methylenedixoy-6-propylphenyl)-5-methyl-1,3-dioxane, piperonyl butoxide, octachlorodipropyl ether, etc. |

Such a synergist can be compounded in the range of about 0.01 to about 0.3 weight part, preferably about 0.02 to about 0.2 weight part per 1 weight part in total of the compound (a) of the formula (I) and the pyrethroid compound (b).

The termite-controlling agent composition of the invention, when used, can be made into usual formulation forms. These forms include, for example, liquids, emulsions, suspensions, powders, foams, pastes, granules, aerosols, active compounds-permeated natural and synthetic materials, microcapsules, etc.

These formulations can be prepared according to processes known per se. For example, the preparation can be carried out by mixing the active compounds with developers (e.g., liquid diluents, liquefied gas diluents, solid diluents or carriers), and, if desired, surfactants (e.g., emulsifiers, dispersants, foaming agents), etc. When water is used as the developer, organic solvents can, for example, be used as an auxiliary solvent.

The liquid diluents or carriers include, for example, aromatic hydrocarbons (e.g., xylene, toluene, alkylnaphthalene, etc.), chlorinated aromatic or chlorinated aliphatic hydrocarbons (e.g., chlorobenzenes, ethylene chlorides, methylene chloride, etc.), aliphatic hydrocarbons (e.g., cyclohexane, etc. and paraffins (e.g., mineral oil fraction, etc.)), alcohols (e.g., butanol, glycol and their ethers and esters, etc.), ketones (e.g., acetone, methyl ethyl ketone, methyl isobutyl ketone, or cyclohexanone, etc.), strongly polar solvents (e.g., dimethylformamide, dimethylsulfoxide, etc.), water, etc.

The liquefied gas diluents are those which gasify at ordinary temperature and atmospheric pressure, and examples thereof are aerosol propellants such as butane, propane, nitrogen gas, carbon dioxide and halogenated hydrocarbons.

The solid diluents include, for example, soil natural minerals (e.g., kaolin, clay, talc, chalk, attapulgite, montmorillonite, diatom earth, etc.), soil synthetic minerals (e.g., highly dispersed silicic acid, alumina, silicate salts, etc.) etc.

As solid carriers for the granules can be mentioned ground and fractionated stones and rocks (e.g., calcite, marble, pumice, sepiolite, dolomite, etc.), synthetic granules of inorganic and organic meals and organic substance powder, fine grains of organic susbstances (e.g, sawdust, the shells of coconuts, the spike axes of corn, stems of tabacco plants, etc.), etc.

The emulsifiers and/or foaming agents include nonionic and ionic emulsifiers (e.g., polyoxyethylene fatty acid esters, polyoxyethylene fatty acid alcohol ethers (e.g., alkyl aryl polyglycol ethers, alkylsulfonate salts, alkyl sulfate salts, arylsulfonate salts, etc.), etc.), albumin hydrolyzates, etc.

The dispersants include, for example, lignin sulfite waste liquids, methylcellulose, etc.

Stickers can also be used in formulations (dusts, granules, emulsions), and include carboxymethylcellulose, natural and synthetic polymers (e.g., gum arabic, polyvinyl alcohol, polyvinyl acetate, etc.), etc.

Colorants can also be used, and include inorganic pigments (e.g., iron oxide, titanium oxide and Prussian blue); organic dyes such as alizarin dyes, azo dyes and metal phthalocyanine dyes; microelements such as iron, manganese, boron, copper, cobalt, molybdenum and zinc and their salts; etc.

Generally, these formulations can each contain the compound (a) of the formula (I) and the pyrethroid compound (b) in the range of 0.001 to 95% by weight, preferably 0.5 to 90% by weight in total. The weight ratio of (a) to pyrethroid may range from 100:1 to 1:1, advantageously from 50:1 to 5:1, and preferably from 25:1 to 10:1.

As apparent from the later-described test example, the composition of the invention has a strong termite-control effect, and can widely be used as a preventive agent or an exterminator on wood, woody plywood, etc. which termites may parasitize in the future or are already parasitizing, or as a treatment agent for soils where termites live or may live in the future.

Examples of termites controllable by the composition of the invention includes:

Deucotermes speratus, Coptoternes forimosanus, Glyptotermes fucus, Glyptermes satsumensis, Glyptotermes nabajimai, Glyptotermes kodamai, Incisitermes minor, Neotermes koshunensis, Glyptotermes domesticus, Hodotermopsis japonica, Reticulitermes miyatakei, Odontotermes formosauns, Nlasutitermes takasagoensis, Capritermes nitobei, etc.

The dosage of the composition of the invention can be varied over a wide range in accordance with the forms of formulation, application places, kinds of termites to be targeted, etc. However generally, the amount can be in the range of about 0.001 g to about 5 g, preferably about 0.002 g to about 3 g per $m^2$ as the total amount of the compound of the formula (I) and the pyrethroid compound.

Application methods for the composition of the invention include, for example, painting, application, etc., and the concentrations of the effective ingredients can be in the range of about 0.0001 to about 0.1% by weight, preferably about 0.0002 to about 0.01% by weight as the total amount of the compound of the formula (I) and the pyrethroid compound.

This invention is further specifically described in the following illustrative examples.

EXAMPLE 1:

Termite-Control Test

A. Test compounds (a) Compounds of the formula (I)
 (a)-1: 1-(6-chloro-3-pyridylmethyl)-2-nitro-imidazolidin-2-ylideneamine
 (a)-2: N'-cyano-N-(2-chloro-5-pyridylmethyl)-N-methylacetamidine (b) Pyrethroid compounds
 (b)-1: cyfluthrin (common name)
 (b)-2: permethrin (common name)

(c) Synergist
 (c)-1: piperonyl butoxide

B. Preparation of test chemical liquids

Solvent: xylol 3 weight parts Emulsifier: polyoxyethylene alkyl phenyl ether 1 weight part In order to prepare a suitable formulation, 1 weight part in total of the compound of the formula (I), the pyrethroid compound and the synergist was mixed with the above-mentioned amount of the solvent containing the above-mentioned amount of the emulsifer, and the mixture was diluted with water to a predetermined concentration to give a test chemical liquid.

C. Test method

Filter paper was placed on glass Petri dishes of diameter 9 cm, and 20 worker-termites and 4 soldier-termites, belonging to *Coptotermes formosanus*, were put in each Petri dish. 4 ml each of the chemical liquids which had been diluted to the predetermined concentrations according to the above method were applied using microsprayers.

The Petri dishes were moved to a constant temperature room of 25° C.; 24 hours after the chemical treatment, the number of dead worker-termites were counted; and the mortality was calculated. This test was carried out in two replicates. The results are shown in the following Table 1.

TABLE I

| Active compound Synergist | Concentrations of effective ingredients (ppm) | Insecticidal rate after 24 hours (%) |
|---|---|---|
| (a)-1 + (b)-1 | 40 + 1.6 | 95 |
|  | 40 + 0.8 | 93 |
|  | 8 + 1.6 | 90 |
|  | 8 + 0.8 | 78 |
| (a)-1 + (b)-1 + (c)-1 | 8 + 0.8 + 1.6 | 95 |
| (a)-2 + (b)-1 | 8 + 1.6 | 100 |
|  | 8 + 0.8 | 95 |
|  | 1.6 + 1.6 | 90 |
|  | 1.6 + 0.8 | 88 |
| (a)-1 + (b)-2 | 40 + 1.6 | 95 |
|  | 40 + 0.8 | 95 |
|  | 8 + 1.6 | 90 |
|  | 8 + 0.8 | 88 |
| (a)-1 | 40 | 65 |
|  | 8 | 8 |
| (a)-2 | 8 | 78 |
|  | 1.6 | 60 |
| (b)-1 | 1.6 | 33 |
|  | 0.8 | 20 |
| (b)-2 | 1.6 | 25 |
|  | 0.8 | 20 |
| (c)-1 | 1.6 | 0 |
| Untreated |  | 0 |

The following examples illustrate suitable formulations:

EXAMPLE 2:

Oil Solution

|  | wt % |
|---|---|
| Active Compound (a)- (described in Ex. 1) | 10.004 |
| Cyfluthrin (common name) | 0.00016 |
| Tebuconazol (common name) | 1.2 |
| Dipropylene glycol monomethyl ether | 10.0 |
| Odorless kerosene | 88.79584 |

The above components are mixed to give an oil solution.

EXAMPLE 3:

Emulsion

|  | wt % |
|---|---|
| Active Compound (a)-1 (described in Ex. 1) | 0.1 |
| Cyfluthrin (common name) | 0.004 |
| Polyoxyethylene tristyryl phenyl ether | 4.0 |
| Calcium dodecylbenzenesulfonate | 1.0 |
| Xylene | 94.896 |

The above components are mixed by stirring to give an emulsion.

It will be understood that the specification and examples are illustrative but not limitative of the present invention and that other embodiments within the spirit and scope of the invention will suggest themselves to those skilled in the art.

We claim:

1. A termite-controlling composition comprising a synergistic termite-controlling effective amount of the following components:

a) N-cyano-N'-(2-chloro-5-pyridylmethyl)-N'-methylacetamidine; and b) cyfluthrin;

and the composition further comprises an inert carrier.

2. A method of combatting termites which comprises applying to said termites or to a termite-infested habitat an effective amount therefor of a termite-controlling composition according to claim 1.

* * * * *